(12) United States Patent
Igarashi et al.

(10) Patent No.: US 8,715,921 B2
(45) Date of Patent: May 6, 2014

(54) METHOD OF DIAGNOSING APOPLECTIC STROKE/ASYMPTOMATIC BRAIN INFARCTION USING ACROLEIN CONTENT

(76) Inventors: Kazuei Igarashi, Chiba (JP); Shiro Ueda, Chiba (JP); Naokatsu Saeki, Chiba (JP); Keiko Kashiwagi, Chiba (JP); Hideyuki Tomitori, Chiba (JP)

( * ) Notice: Subject to any disclaimer, the term of this patent is extended or adjusted under 35 U.S.C. 154(b) by 1488 days.

(21) Appl. No.: 10/599,221

(22) PCT Filed: Mar. 25, 2005

(86) PCT No.: PCT/JP2005/006429
§ 371 (c)(1),
(2), (4) Date: Apr. 29, 2008

(87) PCT Pub. No.: WO2005/093412
PCT Pub. Date: Oct. 6, 2005

(65) Prior Publication Data
US 2008/0254495 A1    Oct. 16, 2008

(30) Foreign Application Priority Data

Mar. 25, 2004 (JP) ................................. 2004-089063
Sep. 2, 2004 (JP) ................................. 2004-255976

(51) Int. Cl.
*C12Q 1/00* (2006.01)

(52) U.S. Cl.
USPC ............................................. 435/4; 435/25

(58) Field of Classification Search
USPC ....................................................... 435/4, 25
See application file for complete search history.

(56) References Cited

FOREIGN PATENT DOCUMENTS

| JP | 2002-181820 | 6/2002 |
| JP | 2002-520360 | 7/2002 |
| JP | 2002-281999 | 10/2002 |
| WO | WO 00/03711 | 1/2000 |

OTHER PUBLICATIONS

Ivanova et al. "Neuroprotection in cerebral ischemia by neutralization of 3-aminopropanal", PNAS, 2002, 99(8):5579-5584.*
Ivanova et al. "Cerebral ischemia enhances polyamine oxidation: identification of enzymatically formed 3-aminopropanal as an endogenous mediator of neuronal and glial cell death", J. Exp. Med. 1998, 188(2):327-340.*
Ivanova et al. "Neuroprotection in cerebral ischemia by neutralization of 3-aminopropanal", Proc. Nat. Acad. Sci., USA, 2002, 99(8):5579-5584.*
Sakata et al. "Acrolein produced from polyamines as one of the uraemic toxins", Biochemical Society Transactions, 2003, 31(2):371-374.*
Els T; Bruckmann J; Rohn G; Daffertshofer M; Monting J S; Ernestus R I; Hennericic M: "Spermidine: A predictor for neurological outcome and infarct size in focal cerebral ischemia?" Stroke; A Journal of Cerebral Circulation Jan. 2001, vol. 32, No. 1 Jan. 2001, pp. 43-46, XP002542634 ISSN: 1524-4628.
De Verna N; Camon L; Martinez E: "Polyamines and brain injury." Amino Acids (Vienna) vol. 12, No. 1, 1997, pp. 1-7, XP009121781 ISSN: 0939-4451 * polyamines in cerebral ischemia. *.
Adibhatla Rao Muralikrishna; Hatcher James F; Sailor Kurt; Dempsey Robert J: "Polyamines and central nervous system injury: spermine and spermidine decrease following transient focal cerebral ischemia in spontaneously hypertensive rats." Brain Research May 31, 2002, vol. 938, No. 1-2, May 31, 2002, pp. 81-86, XP009121771 ISSN: 0006-8993.
Sakata Kaori; Kashiwagi Keiko; Sharmin Shahana; Ueda Shiro; Irie Yasubumi; Murotani Noriyoshi; Igarashi Kazuei: "Increase in putrescine, amine oxidase, and acrolein in plasma of renal failure patients." Biochemical and Biophysical Research Communications May 23, 2003, vol. 305, No. 1, May 23, 2003, pp. 143-149 XP009121767 ISSN 0006-291X.
Tomitori Hideyuki; Usui Teruyoshi; Saeki Naokatsu; Ueda Shiro; Kase Hiroshi; Nishimura Kazuhiro; Kashiwagi Keiko; Igarashi Kazuei: "Polyamine oxidase and acrolein as novel biochemical markers for diagnosis of cerebral stroke." Stroke; A Journal of Cerebral Circulation Dec. 2005, vol. 36, No. 12, Dec. 2005, pp. 2609-2613, XP009121762 ISSN: 1524-4628.
Sharmin, et al., "Polyamine Cytotoxicity in the Presence of Bovine Serum Amine Oxidase", Biochemical and Biophysical Research Communications 282, 228-235 (2001).

* cited by examiner

*Primary Examiner* — Bin Shen
(74) *Attorney, Agent, or Firm* — Beverly W. Lubit; Greenberg Traurig, LLP

(57) ABSTRACT

The present invention provides a diagnostic method for stroke/asymptomatic cerebral infarction and a screening method for patients with stroke/asymptomatic cerebral infarction, which comprise measuring acrolein content or polyamine content; or polyamine oxidase activity or protein content of polyamine oxidase in plasma. The knowledge of the present invention indicates the possibility of preventing, inhibiting the progression of stroke/asymptomatic cerebral infarction by inhibiting polyamine oxidase, and the possibility of obtaining a therapeutic agent for stroke/asymptomatic cerebral infarction by searching for compounds that inhibit polyamine oxidase.

16 Claims, 4 Drawing Sheets

A

B

C

METHOD OF DIAGNOSING APOPLECTIC STROKE/ASYMPTOMATIC BRAIN INFARCTION USING ACROLEIN CONTENT

This application is a national stage filing under 35 U.S.C. 371 of International Application PCT/JP2005/006429, filed on Mar. 25, 2005, which claims the benefit of Japanese Application No: 2004-89063, filed on Mar. 25, 2004 and Japanese Application No: 2004-255976, filed Sep. 2, 2004. The entire teachings of the referenced Applications are incorporated herein by reference. International Application PCT/JP2005/006429 was published under PCT Article 21(2) in English.

BACKGROUND OF THE INVENTION

1. Field of the Invention

The present invention relates to a diagnostic method for stroke/asymptomatic cerebral infarction using polyamine or acrolein content, polyamine oxidase activity or protein content thereof as an indicator. Furthermore, the present invention relates to a screening method for patients with stroke/asymptomatic cerebral infarction using polyamine or acrolein content, polyamine oxidase activity or protein content thereof as an indicator.

2. Description of the Related Art

Cerebrovascular disease is the common cause of death next to malignant neoplasm and cardiac disease, and the annual loss of life number thereof is around 10 times of that of renal disease. Moreover, it causes such a tremendous trouble in daily life, for aftereffect of the disease accompanies paralysis and akinesia for example. Stroke constitutes a majority of the cerebrovascular diseases, and early detection and treatment of the disease are difficult. Furthermore, asymptomatic brain infarction that does not show any subjective symptoms is mostly detected accidentally by diagnostic imaging. So, in present circumstances, there have been no diagnostic markers available in blood or urine examination. Therefore, development of a simple and accurate diagnostic method, which does not require expensive medical equipments such as diagnostic imaging system, has been desired.

By the way, polyamine is biogenic amine that exists in the body universally, and spermine, spermidine or putrescine is the representatives. And these polyamines exist in high concentration in cells and act as cell growth factors by interacting with nucleic acids within the body. On the other hand, polyamine produces cytotoxic acrolein ($CH_2=CH-CHO$) during its metabolic process. This acrolein is detoxified by aldehyde dehydrogenase in cells, but it shows intense toxicity when it leaks out of cells.

In addition, since polyamine accumulates in the plasma of patients with chronic renal failure, it is assumed that polyamine is one of the causative substances of uremia. Moreover, it is said that it is difficult to remove this polyamine by dialyses thoroughly. Thus, clarification the essence of polyamine-induced toxicity leads to the development of more effective therapeutic agents of uremia.

Based on this standpoint, the present inventors tried to inhibit polyamine oxidase, which acts in the pathway for the synthesis of acrolein from polyamine, by using amino guanidine. And as a result, it was confirmed that the polyamine lost its toxicity (Japanese Patent Publication No. 2002-281999). In diseases that involve tissue destruction, it is possible with high probability that polyamine liberated from cells receives oxidative deaminated by polyamine oxidase in plasma, then acrolein is formed in large quantities, so that the formed acrolein is associated with toxicity.

SUMMARY OF TUE INVENTION

As described above, it was known that acrolein generated by oxidative degradation of polyamine is involved in uremia in kidney diseases. However, there has not been sufficient knowledge on whether acrolein is involved in other cerebrovascular diseases such as stroke. The term "stroke" represents local neuropsychiatric symptoms that occur acutely during the course of a pathologic process of cerebral blood vessel, and cerebral infarction and intracerebral bleeding are fundamental as causative diseases. Therefore, the problem to be solved by the present invention is to examine whether or not some quantitative change occurs in the polyamine or acrolein content. If acrolein content changes in patients with stroke, then diagnosis of stroke/asymptomatic cerebral infarction using acrolein as an indicator will be enabled. Moreover, since polyamine oxidase in plasma is involved in the process of the synthesis of acrolein from polyamine, examination on whether some change in polyamine oxidase activity and protein content thereof occurs or not is also the problem to be solved by the present invention.

The present inventors measured the acrolein content, the polyamine content and the polyamine oxidase activity in plasma of the subjects, and then compared on the difference between stroke/asymptomatic cerebral infarction group and healthy group or group of other brain disease. As a result, this study confirmed that acrolein content and polyamine oxidase activity in plasma were obviously high in the stroke/asymptomatic cerebral infarction group, compared with the healthy group or the group of other brain diseases. Further still, the inventors confirmed that infarction is found in subjects with high acrolein content and polyamine oxidase activity in plasma, by taking head tomographic images of the subjects using magnetic resonance imaging (MRI), and thus the present invention was completed.

In other words, the present invention provides a diagnostic method for discovering and predicting stroke/asymptomatic cerebral infarction. According to the present invention, by measuring acrolein content, polyamine oxidase activity or protein content of polyamine oxidase, or polyamine content in plasma, stroke/asymptomatic cerebral infarction can be predicted and discovered.

The present invention provides a diagnostic method for stroke/asymptomatic cerebral infarction and a screening method for patients with stroke/asymptomatic cerebral infarction by measuring acrolein content, polyamine content, or polyamine oxidase activity or protein content thereof. The knowledge of the present invention indicates the possibility of preventing stroke/asymptomatic cerebral infarction or inhibiting the progression of the diseases by blocking the pathway for the synthesis of acrolein from polyamine in vivo by way of polyamine oxidase mediated oxidative deamination. The knowledge of the present invention further indicates the possibility of obtaining therapeutic agents for stroke/asymptomatic cerebral infarction by searching for compounds that inhibit polyamine oxidase, therefore various application can be achieved.

BEST MODE FOR CARRYING OUT THE INVENTION

Figure 1:
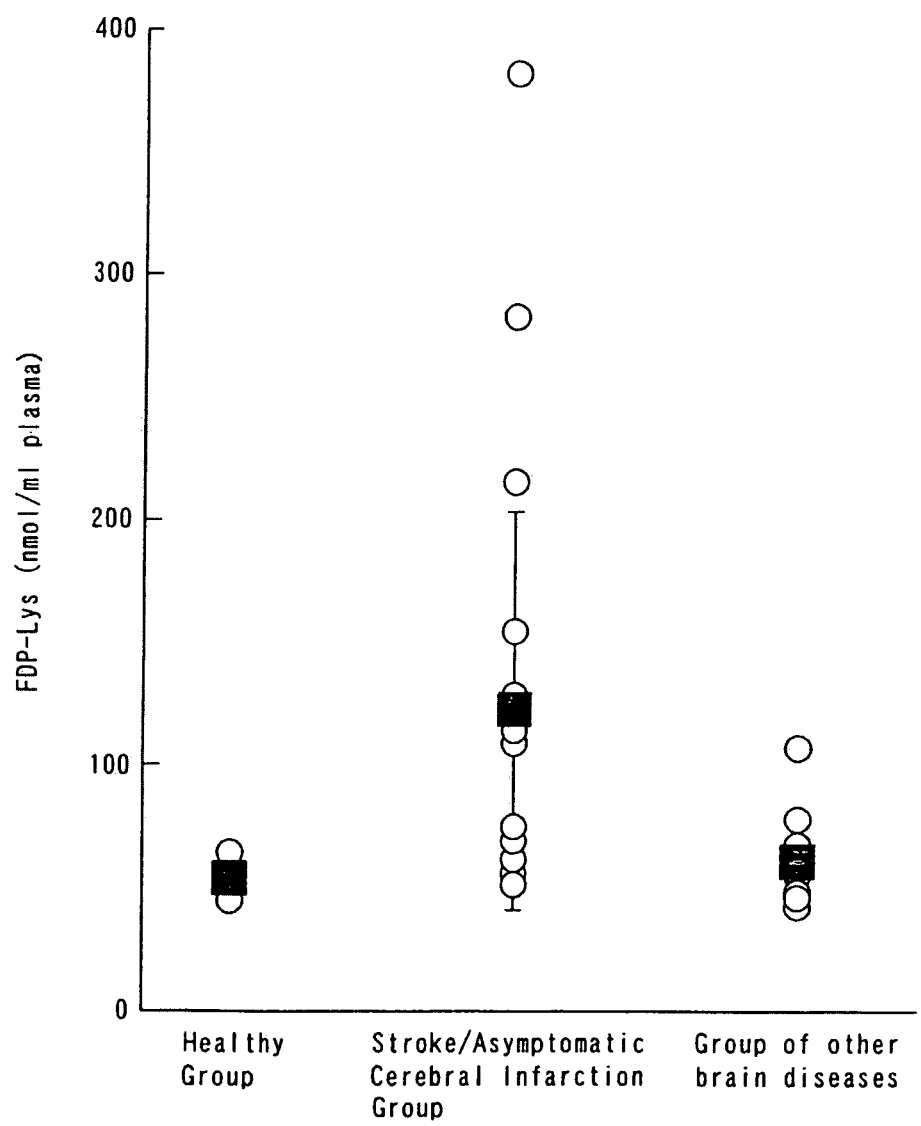
FIG. 1 is a graph showing comparison of FDP-lysine content in plasma among the stroke/asymptomatic cerebral infarction group, the healthy group and the group of other brain diseases.

In the present invention, the inventors found that acrolein, formed by the oxidative degradation of polyamine, exist in blood serum of the patients with cerebral infarction and intracerebral hemorrhage. In addition, the inventors proved that the increase in acrolein content, polyamine content and polyamine oxidase activity could be used as a means for discovering or predicting cerebral infarction and intracerebral hemorrhage.

Therefore, the present invention provides a diagnostic method for stroke/asymptomatic cerebral infarction, which comprises sampling biological sample from subject, measuring polyamine content or aldehyde compound content formed from the polyamine in the sample; or polyamine oxidase activity or protein content of polyamine oxidase in the sample, and diagnosing stroke/asymptomatic cerebral infarction using the measured value obtained as an indicator. Also, the present invention provides a screening method for patients with stroke/asymptomatic cerebral infarction, which comprises sampling biological sample from subject, measuring polyamine content or aldehyde compound content formed from the polyamine in the sample; or polyamine oxidase activity or protein content of polyamine oxidase in the sample, and screening for patients with stroke/asymptomatic cerebral infarction using the measured value obtained as an indicator.

In the present invention, at first, biological samples for measurement are taken from subjects. Biological samples used in the present invention may preferably be the blood plasma used in the following example. However, other biological samples, such as urine, saliva, cerebrospinal fluid and bone marrow fluid can also be used.

The term "polyamine" herein represents a straight-chain aliphatic hydrocarbon having two or more primary amino groups. Known biogenic polyamines may include, but are not limited to, putrescine, cadaverine, spermidine, spermine, 1,3-diaminopropane, caldine, homospermidine, 3-aminopropylcadaverine, norspermine, thermospermine, caldopentamine, and so on. Meanwhile, preferred polyamines in the present invention may be putrescine, spermidine and spermine.

The above polyamines are metabolized by oxidation, acetylation, transamination and carbamoylation, and polyamine oxidase is the enzyme that involves in the oxidation of polyamine. The term "polyamine oxidase" herein represents an enzyme that oxidizes diamine or polyamine as a good substrate and generates hydrogen peroxide. Polyamine receives oxidative deamination by polyamine oxidase, thereby aldehyde compounds such as acrolein would be produced. The preferred aldehyde compound in the present invention may be acrolein, but is not so limited to it.

The acrolein content in plasma could be determined by measuring the content of FDP-lysine (N-formyl-piperidino-lysine), which is an amino acid adder with acrolein. FDP-lysine content could be measured by using ACR-LYSINEADDUCT ELISA SYSTEM (NOF CORPORATION), for example, according to the attached manual. In addition, acrolein content could be measured in the form of derivatives other than FDP-lysine. Furthermore, it is also possible to measure acrolein content directly, and such procedure is described in a report by Alarcon et al. (Alarcon R. A. (1968) Anal. Chem. 40, 1704-1708), for example. However, the problem is that the reactivity of acrolein with other molecules is so high that the amount of free acrolein in the blood is very little. Thus, considering the measurement of acrolein in the form of FDP-lysine is simple and easy, it is a preferred embodiment in the present invention to measure acrolein in the form of FDP-lysine.

Specifically, patient serum and standard solution are dispensed into a plate immobilized with antigen by 50 µl/well, and further the same amount of primary antibody solution is added. The fluid is removed after left at rest for 30 minutes at room temperature and washed by a washing solution, and then 100 µl/well of secondary antibody solution is dispended into the plate. It is washed by the washing solution after left at rest for 1 hour at room temperature, and then color was developed by adding coloring reagent and leaving at rest for 15 minutes at room temperature. The absorbance at 450 nm is determined using a plate reader, and the amount of acrolein in plasma is displayed as the amount of FDP-lysine contained in one ml of patient serum (nmol/ml plasma).

The measurement of polyamine oxidase activity can be conducted, as shown in the following examples for example, by incubating 0.15 ml of reaction mixture containing 10 mM Tris-hydrochloric acid (pH 7.5), 0.2 mM substrate (spermine, spermidine and putrescine), and 0.03 ml of patient plasma for 48 hours at 37° C. Trichloroacetic acid (TCA) is added to 0.02 ml of the reaction mixture to a final concentration of 5%, and it is treated by centrifugalization. A part of obtained supernatant is used for polyamine assay. The activity of amine oxidase can be displayed as the amount of spermidine generated by the decomposition of spermine per one ml of patient serum (nmol/ml plasma/48 h).

The methods of measuring the enzyme activity of polyamine oxidase are described in various reports, and report by Sharmin et al. (Sharmin et al., (2001) Biochem. Biophys. Res. Commun. 282, 228-235), report by Sakata et al. (Sakata et al., (2003) Biochem. Biophys Res. Commun. 305, 143-149), and report by Igarashi et al. (Igarashi et al., (1986) J. Bacteriol. 166, 128-134) can be cited as the concrete examples. Based on the description of these reports, those skilled in the art can measure the enzymatic activity of polyamine oxidase by making appropriate modifications.

Furthermore, protein content of polyamine oxidase can be measured by enzyme-linked immunosorbent assay (EILSA), western blotting analysis or immunoprecipitation method using specific antibody for polyamine oxidase, for example. These methods are heretofore known and commonly used, therefore, those skilled in the art can measure protein content of the enzyme using the above methods by setting appropriate conditions ad libitum. In addition, antibodies to polyamine oxidase used for conducting these measurements can be a monoclonal antibody or a polyclonal antibody.

The polyclonal antibody to polyamine oxidase can be obtained by a conventional technique for production of a peptide fragment for example, by immunizing rabbits with the peptide fragment of polyamine oxidase. The production of peptide antibody can be confirmed through assaying whether the antibody has reached to sufficient titer by taking blood from rabbits administered with the peptide and measuring its antibody titer. The methods for producing peptide antibody are described in various experimental manuals and well known among those skilled in the art, so the antibody to polyamine oxidase can be obtained by making various modifications based on those descriptions.

The polyamine content in the samples can be measured by high-performance liquid chromatography (HPLC). For example, in cases where polyamine column commercially available from TOSO can be used, retention time of polyamines (putrescine, spermidine and spermine) on the HPLC is 7 minutes, 12 minutes and 25 minutes, respectively. The amount of polyamine can be represented as the amount of putrescine, spermidine and spermine contained in one ml of patient serum (nmol/ml plasma). Further, other normal amino acid columns can be used ad libitum.

In the following examples, the presence of infarction was examined by obtaining head tomographic image with magnetic resonance imaging diagnosis (MRI) with the consent of subjects. As a result, as shown in the following examples, evidence of cerebral infarction was shown in the subjects who indicated elevated polyamine levels in the healthy group.

Therefore, it was shown in this invention that acrolein content, polyamine content, or polyamine oxidase activity of the cerebral infarction patients in plasma was higher than healthy subjects, and stroke/asymptomatic cerebral infarction could be diagnosed using above measured values as an indicator using the knowledge of this invention. In addition, by utilizing the knowledge obtained in the present invention, the patients of stroke/asymptomatic cerebral infarction can be screened using above measured values as an indicator. For example, by statistical analysis on average and variance of above indicative measured values of the healthy group, upper normal limit of the above measurements are set. Based on those values, it would be possible to diagnose that those subjects showing higher values may be suffering from stroke/asymptomatic cerebral infarction with high probability.

Furthermore, the knowledge of the present invention indicate the possibility of preventing stroke and inhibiting progression of the disease, by suppressing generation of acrolein in a living body, through inhibiting polyamine oxidase activity in plasma. This invention thus provides the possibility of developing a new ground for the treatment of stroke.

Moreover, by administrating a candidate compound that could be effective in the treatment of stroke to experimental animals and measuring whether the compound has the activity of inhibiting polyamine oxidase in plasma of said animals, it would be possible to search a new medicine effective in the treatment of stroke. Therefore, this invention also provides a new way to search for novel effective medicines for treatment of stroke.

EXAMPLES

Hereinafter, the present invention will be further concretely described with some examples, but the invention is not so limited within the descriptions.

Example 1

Comparison of Acrolein Content in Plasma of Patients with Brain Disorder

Acrolein contents in plasmas of patients with brain disorder were examined. The acrolein contents in the obtained bloods were compared among normal healthy subjects, infarction or intracerebral hemorrhage group, and group of other brain disorder.

The acrolein content in plasma was determined by measuring FDP-lysine (N-formyl-piperidino-lysine), which is an amino acid added with acrolein. It was measured by using ACR-LYSINEADDUCT ELISA SYSTEM (NOF CORPORATION), according to the attached manual. Patient serum and standard solution were dispensed by 50 µl/well into a plate immobilized with antigen, and further the same amount of primary antibody solution was added. The fluid was left at rest for 30 minutes at room temperature, then it was removed and washed by washing solution. Afterward, coloring reagent was added and it was left at rest for 15 minutes at room temperature for color development. Absorbance was determined at 450 nm by plate reader. The amount of acrolein in plasma was represented as the content of FDP-lysine per milliliter of patient serum (nmol/ml plasma).

As shown in FIG. 1, FDP-lysine content that reflects acrolein content in plasma was highest in the infarction or intracerebral hemorrhage group among the above three groups, and the increase was significant compared with other groups. In addition, by comparing with acrolein content in plasma of patients with renal failure, it was revealed that FDP-lysine content of infarction patients increased to the same level as renal failure patients.

Example 2

Figure 2:
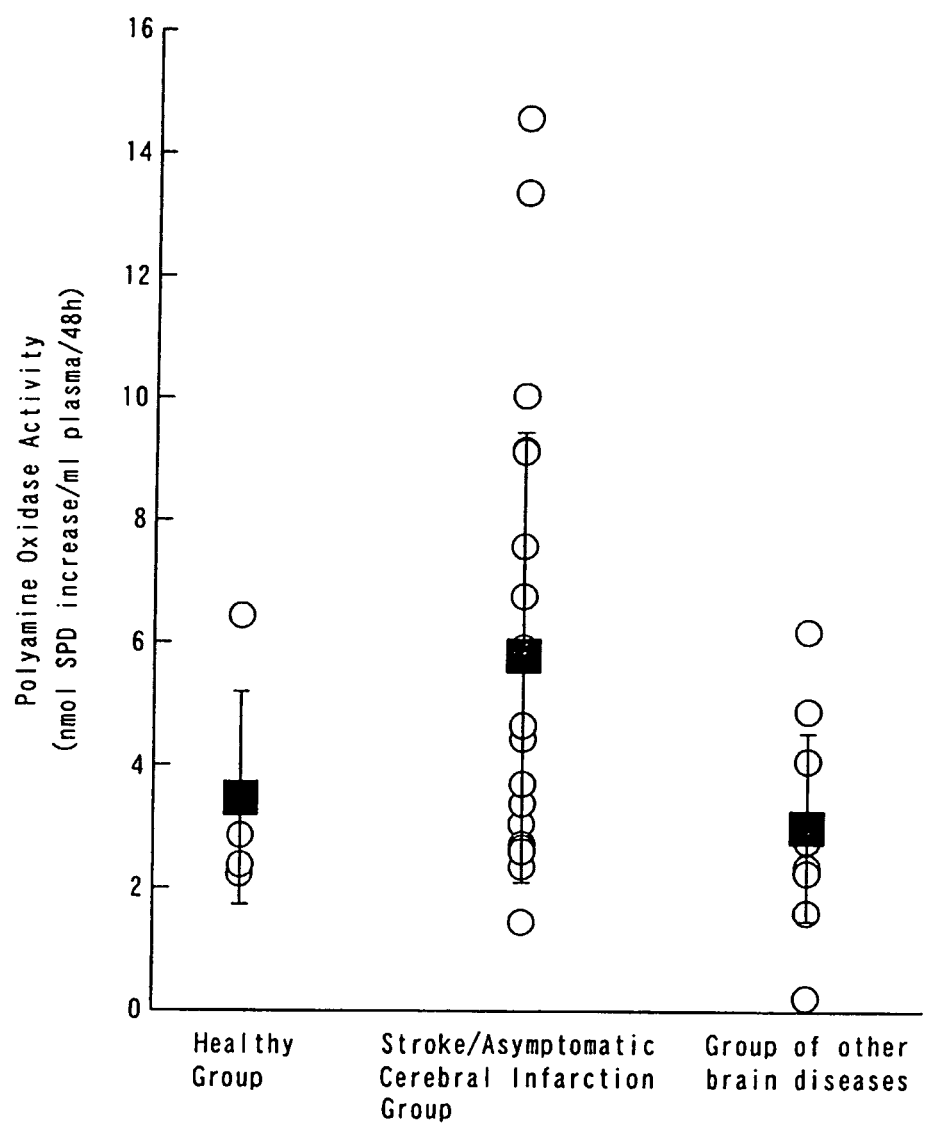
FIG. 2 is a graph showing comparison of polyamine oxidase activity in plasma among the stroke/asymptomatic cerebral infarction group, the healthy group and the group of other brain diseases.

Comparison of Amine Oxidase Activity in Plasma of Patients with Infarction Disorder The polyamine oxidase activity in the plasma of patients used in example 1 was measured. The results are shown in FIG. 2. The polyamine oxidase activity in the plasma was measured by incubating 0.15 ml of reaction mixture containing 10 mM Tris-hydrochloric acid (pH 7.5), 0.2 mM substrate (spermine, spermidine and putrescine), and 0.03 ml of patient plasma at 37° C. for 48 hours, Trichloroacetic acid (TCA) was added to 0.02 ml of the reaction mixture to a final concentration of 5%, and it was treated by centrifugalization. A part of obtained supernatant was used for polyamine assay. The activity of amine oxidase was represented as the amount of spermidine generated by the decomposition of spermine per milliliter of patient serum (nmol/ml plasma/48 h).

The polyamine oxidase activity in plasma of infarction or intracerebral hemorrhage group was significantly higher compared with healthy subjects and the group of other brain disorder. This result correlated with acrolein content in plasma examined in example 1.

Example 3

Analysis of Head Tomographic Image by Magnetic Resonance Imaging Diagnosis (MRI)

Figure 3:
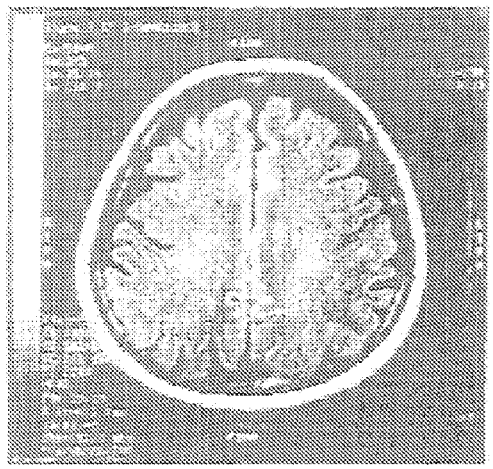
FIG. 3 is a photograph showing the result of head tomographic image analysis using MRI.
Figure 3:
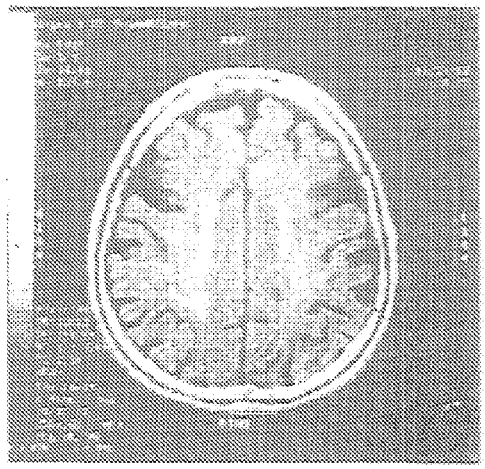
Figure 3:
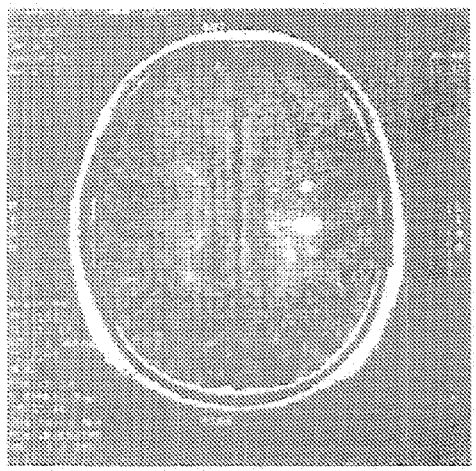

The presence of infarction was examined by taking head tomographic image by MRI with the permission and consent of subjects. The MRI tomographic images are shown on healthy subjects (FIG. 3A), patients with brain infarction (FIG. 3B), and subjects with extremely high level of acrolein content and polyamine oxidase activity in plasma whose disease names have not been established (FIG. 3C). As shown in FIG. 3C, in patients with increased level of acrolein and polyamine oxidase activity in plasma, multifocal infarction was found in bilateral frontal, temporal and parietal lobes and basal ganglion. In addition, atrophy and arteriosclerosis of brain were found.

Example 4

Figure 4:
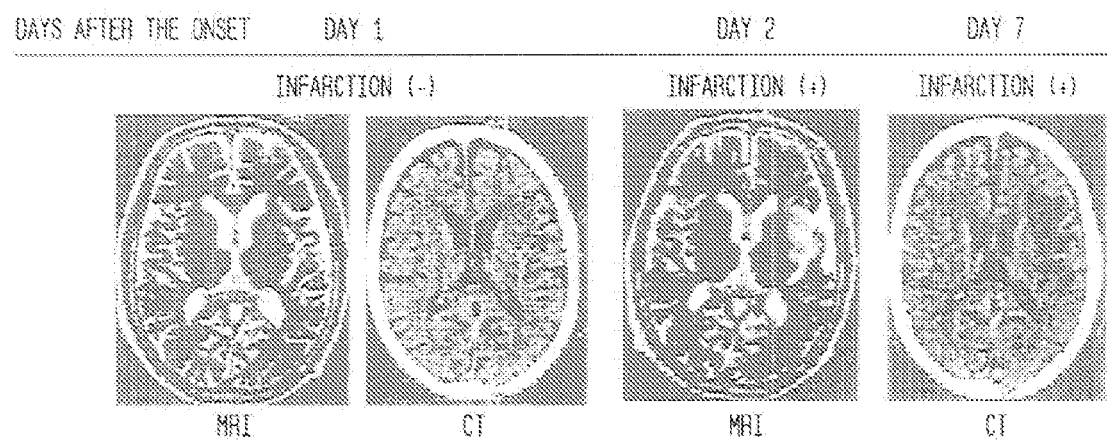
FIG. 4 is a photograph examining on the time course of head tomographic image analysis using MRI and CT.

Comparison of Changes in Head Tomographic Images, Polyamine Oxidase Activity and Acrolein Content in Plasma in Patients in the Acute Stage of Brain Infarction For one patient in the acute stage of brain infarction, changes in head tomographic images (MRI and CT) and the accompanied changes in the polyamine oxidase activity and acrolein content in plasma were analyzed on day 1, day 2 and day 7 after the onset of stroke. The photographs of head tomographic images are shown in FIG. 4. On the day of the onset, definitive evidence of infarction was not found in T2-weighted MRI and CT. On the other hand, the polyamine oxidase activity and FDP-Lys content in plasma on the day of the onset was 6.6 nmol SPD/ml plasma and 18.4 nmol/ml plasma, respectively. These results revealed that plasma polyamine oxidase activity was about twice as high as that of healthy subjects, and significantly high. Definitive evidence of infarction was found in the left temporal lobe in the magnetic resonance imaging (MRI) of the second day of the onset and in the head computed tomography (CT) after one week of the onset. The polyamine oxidase activity and FDP-Lys content in plasma after one week of the onset was 7.2 nmol SPD/ml plasma and 23.0 nmol/ml plasma, respectively. Therefore, along with the increase in plasma polyamine oxidase activity, significant increase in acrolein content in plasma was also recognized. As indicated above, it was confirmed that in patients in the acute stage of brain infarction, the increase in polyamine oxidase activity in plasma precedes the emergence of the infarction image in MRI or CT.

INDUSTRIAL APPLICABILITY

The method of the present invention, which comprise measuring acrolein content, polyamine content, polyamine oxidase activity or protein content of polyamine oxidase in plasma, is useful for diagnosing stroke/asymptomatic cerebral infarction and screening for patients with stroke/asymptomatic cerebral infarction. In addition, by utilizing the knowledge of the present invention and inhibiting the pathway for the synthesis of acrolein from polyamine in vivo through polyamine oxidase mediated oxidative deamination, it is possible to prevent stroke/asymptomatic cerebral infarction or inhibiting the progression of the disease. Furthermore, by utilizing the knowledge of the present invention and searching for compounds that inhibit polyamine oxidase, it is possible to obtain therapeutic agents for stroke/asymptomatic cerebral infarction.

The invention claimed is:

1. A diagnostic method for asymptomatic cerebral infarction, comprising:
   (a) obtaining at least one biological sample from a subject;
   (b) measuring biogenic polyamine content in the biological sample; wherein a measure of biogenic polyamine content is at least two measures selected from a measure of polyamine content in the biological sample; a measure of aldehyde compound content formed from the polyamine in the biological sample; a measure of polyamine oxidase activity in the biological sample; and a measure of polyamine oxidase protein content in the biological sample; and
   (c) comparing the biogenic polyamine content of the biological sample in (b) to polyamine content of a biological sample of a healthy subject, wherein a difference in measured value of the subject in (a) compared to a measured value of a healthy subject is indicative of an asymptomatic cerebral infarction.

2. The method according to claim 1, wherein the at least one biological sample is at least one selected from plasma, urine, saliva, cerebrospinal fluid, and bone marrow fluid.

3. The method according to claim 1, wherein the biogenic polyamine is metabolized by at least one of oxidation, acetylation, transamination and carbamoylation.

4. The method according to claim 1, wherein the biogenic polyamine is oxidatively deaminated by polyamine oxidase to produce an aldehyde compound.

5. The method according to claim 1, wherein the aldehyde compound is acrolein.

6. The method according to claim 1, wherein the biogenic polyamine is at least one selected from putrescine, cadaverine, spermidine, spermine, 1,3-diaminopropane, caldine, homospermidine, 3-aminopropylcadaverine, norspermine, thermospermine, and caldopentamine.

7. The method according to claim 1, wherein the biogenic polyamine is at least one of putrescine, spermidine and spermine.

8. The method according to claim 1, wherein the at least two measures of biogenic polyamine content comprise a measure of polyamine content and a measure of polyamine oxidase activity.

9. A screening method to identify a subject that has experienced an asymptomatic cerebral infarction, comprising:
   (a) obtaining at least one biological sample from the subject;
   (b) measuring biogenic polyamine content in the biological sample; wherein a measure of biogenic polyamine content is at least two measures selected from a measure of polyamine content in the biological sample; a measure of aldehyde compound content formed from the polyamine in the biological sample; a measure of polyamine oxidase activity in the biological sample; and a measure of polyamine oxidase protein content in the biological sample; and
   (c) comparing the difference between the measured biogenic polyamine content in (b) to a measured biogenic polyamine content of a healthy subject; wherein the difference in measured value in (c) is indicative of an asymptomatic cerebral infarction.

10. The method according to claim 9, wherein the at least one biological sample is at least one selected from plasma, urine, saliva, cerebrospinal fluid, and bone marrow fluid.

11. The method according to claim 9, wherein the biogenic polyamine is metabolized by at least one of oxidation, acetylation, transamination and carbamoylation.

12. The method according to claim 9, wherein, the biogenic polyamine is oxidatively deaminated by polyamine oxidase to produce an aldehyde compound.

13. The method according to claim 12, wherein the aldehyde compound is acrolein.

14. The method according to claim 9, wherein the biogenic polyamine is at least one selected from putrescine, cadaverine, spermidine, spermine, 1,3-diaminopropane, caldine, homospermidine, 3-aminopropylcadaverine, norspermine, thermospermine, and caldopentamine.

15. The method according to claim 9, wherein the biogenic polyamine is at least one of putrescine, spermidine and spermine.

16. The method according to claim 9, wherein the at least two measures of biogenic polyamine content comprise a measure of polyamine content and a measure of polyamine oxidase activity.

* * * * *